(12) United States Patent
Horwitz

(10) Patent No.: US 6,200,952 B1
(45) Date of Patent: *Mar. 13, 2001

(54) COMBINATION THERAPY METHOD FOR TREATING CHRONIC HEPATITIS B

(75) Inventor: David L. Horwitz, Hillsborough, CA (US)

(73) Assignee: SciClone Pharmaceuticals, Inc., San Mateo, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/363,558

(22) Filed: Dec. 22, 1994

Related U.S. Application Data

(63) Continuation of application No. 08/068,338, filed on Jun. 2, 1993, now abandoned.

(51) Int. Cl.[7] .................................................. A61K 38/16
(52) U.S. Cl. ............................. 514/12; 514/21; 530/324; 530/351
(58) Field of Search ................................ 514/12, 21, 45, 514/49; 530/324

(56) References Cited

U.S. PATENT DOCUMENTS

| | | | |
|---|---|---|---|
| 4,079,127 | * | 3/1978 | Goldstein ............................. 424/177 |
| 4,666,892 | * | 5/1987 | Fox ....................................... 514/49 |
| 4,855,407 | | 8/1989 | Wang .................................. 530/334 |
| 5,215,970 | * | 6/1993 | Datema ................................ 514/49 |
| 5,432,165 | * | 7/1995 | Adair .................................... 514/50 |
| 5,473,063 | * | 12/1995 | Classon ............................... 536/122 |
| 5,559,100 | * | 9/1996 | Koszalka ............................. 514/45 |
| 5,576,429 | * | 11/1996 | Johansson ......................... 536/26.8 |
| 5,849,696 | * | 12/1998 | Chretien .............................. 514/12 |

FOREIGN PATENT DOCUMENTS

| | | |
|---|---|---|
| WO 92/17199 | 10/1992 | (WO). |
| WO 94/01125 | 1/1994 | (WO). |

OTHER PUBLICATIONS

"Sustained Response To Thymosin Therapy In Patients With Chronic Hepatitis B.," Mutchnick, M.G., et al., *Hepatology 16*, Oct. 1992 No. 2, pt. 2), p. 66A.

"Approaches to the Treatment of Hepatitis B Virus and Delta–Related Liver Disease," Thomas, H.C., Ph.D., et al., *Seminars In Liver Disease*, vol. 6, No. 1, 1986 (Thieme, Inc.), pp. 34–41.

"Thymosin: An Innovative Approach To The Treatment Of Chronic Hepatitis B,"Mutchnick, Milton, G., et al., *Combination Therapies*, 1992 (Pienum Press), pp. 149–157.

"Natural History and Therapy of Chronic Hepatitis B Virus Infection," Alexander, Graeme J.M., et al., *The American Journal of Medicine*, vol. 85 (suppl. 2A), Aug. 29, 1988, pp. 143–146.

Peters, M., et al., *Hepatology* (*United States*), (May 1961), 13(5):977–94).

Thomas, H.C., et al., *Seminars In Liver Disease* (1986), 6(1):34–41.

Aach, R.D., et al., *Ann. Int. Med.* (1988), 109:89–91.
Perrillo, R.P., et al., *Ann. Int. Med.* (1988), 109:95–100.
Hoofnagle, J.H., et al., *Gastroenterology* (1988), 95:1318–1325.

* cited by examiner

Primary Examiner—Christopher S. F. Low
Assistant Examiner—David Lukton
(74) Attorney, Agent, or Firm—Townsend and Townsend and Crew LLP

(57) ABSTRACT

The present invention is aimed at augmenting the success rate of using thymosin in treatment of chronic hepatitis B, by employing a combination therapy using thymosin with antiviral agents which are effective in inhibiting DNA synthesis or DNA polymerase during replication of the hepatitis B virus.

3 Claims, No Drawings

COMBINATION THERAPY METHOD FOR TREATING CHRONIC HEPATITIS B

This is a Continuation of application Ser. No. 08/068,338, filed Jun. 2, 1993, now abandoned.

TECHNICAL FIELD

The instant invention relates to a method for treating chronic hepatitis B infections. More specifically, the instant invention relates to a method for treating chronic hepatitis B infections using both thymosin and an antiviral drug.

BACKGROUND OF THE INVENTION

Hepatitis B is the most prevalent form of hepatitis and is the second most common infectious disease worldwide. Worldwide estimates of those chronically infected with hepatitis B virus (HBV) are in excess of 300,000,000. The disease is caused by the hepatitis B virus, a DNA virus. The virus is transmitted through blood transfusions, contaminated needles, sexual contact and vertical transmission from mother to child. Moreover, a significant number of people are infected by unknown means.

Carriers of the virus can exhibit various forms of disease, one of which is chronic hepatitis B. Approximately 50% of the carriers show chronic inflammatory changes in the liver and, of these, about 50% have histopathologic changes, which are termed "chronic active hepatitis", that may lead to fibrosis and ultimately to cirrhosis and progressive liver failure. Carriers without chronic inflammatory changes may also develop chronic active hepatitis. Liver cancer develops in about 10 to 30% of hepatitis B carriers. It has been estimated that approximately 4 million carriers of hepatitis B virus die each year from liver cancer or cirrhosis.

The persistent infection seen in individuals exhibiting chronic hepatitis may be due to a defective or physiologically immature immunological response, resulting in an impaired ability to clear the virus. Although the mechanisms responsible for liver damage are poorly understood, it is thought that in most individuals such damage results from attack by the body's immune system on infected liver cells, rather than from liver destruction by HBV. Cytotoxic T cells appear to be responsible for immune-mediated hepatic damage. The balance between suppression of immune system activity against normal tissue and the immunological response mounted against the virus, also appears to be impaired in chronic hepatitis B. A number of specific immune defects have been described in chronic hepatitis, including defective production of alpha-interferon by HBV-infected hepatocytes and inhibition of cytotoxic T cell responses. (reviewed in Peters, M. et al., *Hepatology* (*United States*) (May 1991) 13(5):977–94).

Chronic infection is manifested by persistence of hepatitis B surface antigen ($HB_sAg$) in the serum for more than 6 months. The presence of hepatitis $B_e$ antigen ($HB_eAg$) is associated with high levels of viral replication.

The goals of treatment in chronic HBV infection include sustained reduction of HBV replication (loss of $HB_eAg$ and HBV DNA), loss of $HB_sAg$, diminished infectivity, normalization of aminotransferase levels, resolution of hepatic inflammation, improvement in symptoms, and a decreased rate of liver disease progression. The disappearance of $HB_sAg$ from serum, implying termination of the HBV carrier state, has been difficult to achieve with antiviral therapy.

Recent therapeutic trials have been directed towards utilization of anti-viral agents, immunomodulators, immunosuppressives or combinations of these. See, e.g. Thomas, H. C. et al., *Seminars in Liver Disease* (1986) 6(1): 34–41; Alexander, G. J. M. et al., *Am. J. Med.* (1988) 85: 143–146; Aach, R. D. et al., *Ann. Int. Med.* (1988) 109: 89–91. At present, alpha-interferon is the only therapeutic approach that has had regulatory approval in a number of countries. Interferon, however, induces a response in less than 50% of patients with chronic hepatitis B, and has significant side effects that sometimes lead to early cessation of therapy. Such side effects include fever, chills, and headaches, followed by fatigue, anorexia, weight loss, emotional disturbances and in some cases, bone marrow suppression. (Perrillo, R. P. et al., *Ann. Int. Med.* (1988) 109: 95–100; Hoofnagle, J. H. et al., *Gastroenterology* (1988) 95: 1318–1325. Other reported side effects include rigors, alopecia, nausea and vomiting.

Various antiviral agents have been used as sole therapy agents in an attempt to treat chronic hepatitis B infection, including acyclovir, vidarabine, and adenine arabinoside. Sole therapy with these antiviral agents generally has been unsuccessful, either because the agent was highly toxic or resulted in some inhibition of viral replication initially, but failed to sustain viral replication inhibition long-term. See e.g. Alexander, G. J. M. et al., *American J. Med.* (1988), 85-2A: 143–146.

Thymosin alpha-1 is a 28 amino acid peptide. The peptide, originally isolated from calf thymus thymosin fraction 5, is one of several polypeptides present in thymosin fraction 5 which participate in the regulation, differentiation and function of thymic dependent lymphocytes (T-cells). The isolation, characterization and use of thymosin alpha-1 is described, for example, in U.S. Pat. No. 4,079,127.

Although the mechanism(s) by which thymosin alpha-1 mediates its effects is unknown, evidence suggests that it may function through modulation of the immune system. Thymosin alpha-1 has been shown to cause increases in lymphocyte counts and enhance production of gamma-interferon in individuals suffering from chronic active hepatitis B (Mutchnick, M. G. et al., *Hepatology* (1991) 14: 409–415).

Mutchnick, M. G. et al., "Thymosin: An Innovative Approach to the Treatment of Chronic Hepatitis B", in *Combination Therapies,* Garaci, E., Plenum Press, New York 1992, pps. 149–157, also describes the use of thymosin alpha-1 in the treatment of chronic active hepatitis B, that is, patients with evidence of liver injury upon biopsy. In 75% of the patients in the study who received the peptide cleared hepatitis B virus DNA from serum and persistently tested negative for serum HBV DNA after treatment was terminated.

There remains an important need for a therapy for chronic hepatitis B that efficiently and with fewer side effects attacks the virus and modulates the immune response system.

SUMMARY OF THE INVENTION

The present invention is aimed at augmenting the success rate of using thymosin in treatment of chronic hepatitis B, by employing a combination therapy using thymosin with antiviral agents which are effective in inhibiting DNA synthesis or DNA polymerase during replication of the hepatitis B virus.

The present invention provides a method for treating chronic hepatitis B infections. In particular, the present invention relates to a method of treating subjects with chronic hepatitis B infection, by using a combination chemotherapy regimen.

Accordingly, in one embodiment, the present invention is directed to a method for treating chronic hepatitis B infection in mammals comprising administering to a subject having chronic hepatitis B a therapeutically effective amount of at least one thymosin, and an inhibitorily effective amount of at least one hepatitis B virus replication or DNA polymerase inhibitor compound, either free or as a pharmaceutically acceptable salt, in a pharmaceutically acceptable vehicle.

In a particularly preferred embodiment, the thymosin is thymosin alpha-1 and the hepatitis B virus replication or DNA polymerase inhibitor compound comprises a nucleoside analog.

These and other embodiments of the present invention will become apparent by reference to the following description and claims.

DETAILED DESCRIPTION OF THE INVENTION

The present invention provides a method for treating chronic hepatitis B infection in mammals comprising concurrently administering to chronic hepatitis B-infected subjects a therapeutically effective amount of at least one thymosin, and an inhibitorily effective amount of at least one hepatitis B virus replication or DNA polymerase inhibitor compound, either free or as a pharmaceutically acceptable salt, in a pharmaceutically acceptable vehicle, which results in improved or beneficially synergistic clinical effects in such subjects. These combination therapies are more effective than when each is administered as a sole treatment modality.

The term "thymosin" as used herein is intended to include any immunopotentiating polypeptide naturally occurring in the thymus gland or produced by chemical or recombinant means, or fragments derived from any of these polypeptides. "Thymosin" includes, thymosin Fraction Five (TF-5), thymosin alpha-1 and any biologically active peptide fragment (such as C-terminal 4-28 and 15-28, and N-terminal 1-8, 1-14 and 1-20 fragments), analog or derivative of any of those. As used herein, the term "thymosin alpha-1" is intended to refer to the 28-mer described below, with or without the N-acetyl group, as well as biologically active analogs of the sequence (i.e. deletion, substitution and addition mutants), which are substantially homologous to the peptide sequence shown below.

Thymosin Fraction Five (TF-5), originally described by Goldstein et al. (*Proc. Nat'l Acad. Sci. (USA)*, 69:1800–1803 (1972)), is a partially purified extract of bovine thymus containing at least 40 peptide components, 20 of which have been purified to homogeneity or near homogeneity; it contains about 0.6% of thymosin alpha-1. Low, et al., "Thymosins: Structure, Function and Therapeutic Application", *Thymus*, 6:27–42 (1984), incorporated by reference.

A peptide that is "substantially homologous" to thymosin alpha-1 is one in which at least about 30%, preferably at least about 85% to about 90% and most preferably about 95%, of the amino acids match over a defined length of the molecule, with the sequence depicted below.

A "biologically active" fragment or analog of thymosin or thymosin alpha-1, is a fragment or analog of thymosin or thymosin alpha-1, respectively which retains a significant amount of the activity of the native molecule, i.e., which is capable of decreasing serum HBV DNA and/or hepatitis B surface antigen, as described further below.

The term "treatment" or "treating" as used herein refers to either (i) the prevention of infection or reinfection (prophylaxis) or (ii) the reduction or elimination of indicators of chronic hepatitis B.

A "therapeutically effective amount" of thymosin is an amount of the peptide which has the capability of changing the measurable parameters of hepatitis B infection. The parameters that will normally be monitored are serum hepatitis B surface antigen and serum viral DNA. Response is defined as a significant decrease of either of these parameters. An amount of peptide which has the ability of eliciting a response is considered a "therapeutically effective amount." HBV DNA can be monitored using the spot hybridization assay described in Mutchnick, M. G. et al., *Hepatology* (1991) 14:409–415 and Lieberman, H. M. et al., *Hepatology* (1983) 3:285–291, both of which are incorporated by reference herein. Alternatively, the presence of HBV DNA in the blood can be measured using standard PCR technology. See, e.g. U.S. Pat. Nos. 4,683,202 and 4,683,195, incorporated herein by reference in their entirety. HBV DNA can also be detected through use of a commercially available kit from Abbott Laboratories, North Chicago, Ill. Serum hepatitis B surface antigen levels can be monitored using standard RIAs, as described by Mutchnick, M. G. et al., *Hepatology* (1991) 14: 409–415 incorporated herein by reference, or by standard ELISAs.

The present invention relates to a combination therapy using a medicament containing as active ingredient at least one thymosin, either in free form or in the form of a pharmaceutically acceptable salt. The thymosin may be administered alone or mixed with a pharmaceutically acceptable vehicle or excipient.

A most preferred embodiment of the present invention is to use a medicament containing as the thymosin active ingredient, thymosin alpha-1 for the treatment of chronic hepatitis B infection. The native molecule is a 28-mer, having the amino acid sequence shown below:

Ac-Ser-Asp-Ala-Ala-Val-Asp-Thr-Ser-Ser-Glu-Ile-Thr-Thr-Lys-Asp-Leu-Lys-Glu-Lys-Lys-Glu-Val-Val-Glu-Glu-Ala-Glu-Asn-OH.

Thymosin alpha-1, as well as fragments and analogs thereof are easily synthesized using standard methods of peptide synthesis, known to those of skill in the art. U.S. Pat. Nos. 4,148,788 and 4,855,407 describe the solution phase and solid phase synthesis, respectively, of thymosin alpha-1, and are incorporated herein by reference in their entirety. See also, Young, J. D., *Solid Phase Peptide Synthesis*, 2nd ed. (Pierce Chemical Company 1984); and Barany, G. and Merrifield, R. B., *The Peptides: Analysis, Synthesis, Biology*, Vol. 2 (Gross, E. and Meienhofer, J. eds., Academic Press 1980), for a discussion of solid phase peptide synthesis; and Bodansky, M. Principles of Peptide Synthesis (Springer-Verlag 1984); and *The Peptides: Analysis, Synthesis, Biology*, Vol. 1 (Gross, E. and Meienhofer, J. eds., Academic Press 1980), for solution phase peptide synthesis.

Thymosin alpha-1 can also be isolated directly from appropriate tissue expressing thymosin alpha-1, using techniques readily known in the art. This is generally accomplished by first preparing a crude tissue extract which lacks cellular components and several extraneous proteins. The thymosin alpha-1 can be further purified, i.e. by column chromatography, HPLC, immunoadsorbent techniques or other conventional methods well known in the art. U.S. Pat. No. 4,079,127 discloses a method for purifying thymosin alpha-1 from calf thymus and is incorporated herein by reference in its entirety.

Thymosin alpha-1 and fragments or analogs thereof, can also be produced recombinantly using methods well known to those of skill in the art. See, e.g. Sambrook, Fritsch &

Maniatis, *Molecular Cloning: A Laboratory Manual*, 2nd ed. (Cold Spring Harbor Laboratory Press 1989); *Oligonucleotide Synthesis* (M. J. Gait ed. 1984).

Thymosins can also be obtained from commercial sources (e.g. Alpha 1 Biomedicals, Inc., Foster City, Calif.).

Typically, the thymosin compositions are prepared as injectables, either as liquid solutions or suspensions; solid forms suitable for solution in, or suspension in, liquid vehicles prior to injection may also be prepared. The preparation may also be emulsified or the active ingredient encapsulated in liposome vehicles. The active ingredient can be mixed with vehicles containing excipients which are pharmaceutically acceptable and compatible with the active ingredient. Suitable vehicles are, for example, water, saline, dextrose, glycerol, ethanol, or the like and combinations thereof. In addition, if desired, the vehicle may contain minor amounts of substances such as wetting or emulsifying agents or pH buffering agents. Actual methods of preparing such dosage forms are known, or will be apparent to those skilled in the art. See, e.g. *Remington's Pharmaceutical Sciences,* Mack Publishing Company, Easton, Pa., 15th edition, (1975). The composition or formulation to be administered will, in any event, contain a quantity of the peptide adequate to reduce or eliminate HBV DNA and/or HBsAg from the serum of the subject being treated.

Thymosins may be administered orally or parenterally. Parenteral administration may be achieved either intravenously, subcutaneously, or by intramuscular injection. Injectable formulations will contain an effective amount of the active ingredient in a vehicle, the exact amount being readily determined by one skilled in the art. The active ingredient may range from about 1% to about 95% (w/w) of the composition, or even higher or lower if appropriate. The quantity to be administered depends on factors such as the age, weight, health, severity of the condition, duration of treatment required of the subject to be treated, and the other drugs of the combination of the invention that are being concurrently administered.

In the most preferred embodiment of the present formulations of the present invention, between about 300 $\mu$g to about 3000 $\mu$g, preferably between about 900 $\mu$g to about 1200 $\mu$g of thymosin alpha-1 per square meter of body area will be administered. Such dosages can be given once a week up to once a day, preferably two to three times a week for a treatment course of between two months to three years, preferably for about 6 to 12 months. A preferred dosage unit form for pharmaceutical use is 1.6 mg of lyophilized thymosin alpha-1 per vial, and this material is reconstituted prior to use by the addition of diluent. Other effective dosages can be readily established by one of ordinary skill in the art without undue experimentation through routine dose response trials.

Additional formulations which are suitable for other modes of administration include suppositories and in some cases, aerosol, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral compositions may be taken in the form of solutions, suspensions, tablets, pills, capsules, sustained release formulations, or powders, and contain from about 10% to about 95% of the active ingredient, preferably about 25% to about 70%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Controlled or sustained release formulations are made by incorporating the peptide into carriers or vehicles such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. The peptides can also be presented using implanted mini-pumps, well known in the art.

Furthermore, the peptides may be formulated into compositions in either neutral or salt forms. Pharmaceutically acceptable salts include the acid addition salts (formed with the free amino groups of the active peptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as for example, sodium, potassium ammonium, calcium, or ferric hydroxides, and such organic bases as isopropylamine, trimethylamine, 2-ethylamino ethanol, histidine, procaine, and the like.

An inhibitorily effective amount of at least one antiviral agent, particularly hepatitis B virus replication or DNA polymerase inhibitor compound is included in the combination chemotherapy regimen of the present invention. The infectious virion of hepatitis B contains a small, circular DNA molecule that is partly single-stranded and a DNA polymerase that can make the DNA fully double-stranded. Its mechanism of replication involves an RNA intermediate. The antiviral agents which act to inhibit hepatitis B viral replication or inhibit DNA polymerase activity of the present invention comprise purine or pyrimidine nucleoside analogs.

An "inhibitorily effective amount" of an antiviral drug or agent is an amount of the drug which inhibits HBV virus replication, measured by a decrease in viral DNA in the blood, as measured by PCR or other method known in the art.

Antiviral agents of the present invention which are pyrimidine nucleoside analogs include ddI, ddC, AZT and FIAU (fluoro-iodo-arabinofuranosyl-uracil) (see Table below). Antiviral agents of the present invention which are purine nucleoside analogs include acyclovir, ribavirin, ganciclovir, and vidarabine (see Table below). AZT, ddC, ddI and FIAU act as polynucleotide chain terminators. Similarly, acyclovir and other purine analogs act as polynucleotide chain terminators. These analogs act as faulty substrates, thus preventing DNA transcription. The mode of action of ribavirin is most likely interference with viral mRNA, resulting in inhibition of viral replication.

The antiviral agents of the present invention, are given in an appropriate pharmaceutical dosage formulation. The pyrimidine nucleoside analogs of the present invention can be given intravenously or orally to chronic hepatitis B-infected subjects at effective viral inhibiting dosages and according to regimens appropriate to the severity of the disease and clinical factors. However, when given in combination with a thymosin, a lower daily dosage for a subject can be devised according to the clinical parameters and tests listed below. Those with skill in the art will, without undue experimentation, be able to devise dosages depending on the clinical condition of patients and the parameters discussed below.

Further, the thymosin and antiviral agent are administered concurrently in that the treatment administration of each drug overlap in time. Preferably, the antiviral agent is administered first with the administration of thymosin beginning at the same time or within four weeks after the first administration of the antiviral agent. Most preferably, administration of thymosin is begun within one week after administration of the antiviral agent has begun.

The following Table lists various antiviral agents of use in the invention with exemplary modes of action and exemplary dosages and modes of administration.

| | Antiviral Agents | | |
|---|---|---|---|
| NAME | CHEMICAL CLASS | MODE OF ACTION[1] | TYPICAL DOSE[2] |
| Zidovudine (AZT) | Pyrimidine analog | Inhibits viral RNA-dependent DNA polymerase (reverse transcriptase); chain termination during DNA synthesis | 200 mg q4h |
| Acyclovir | Purine analog | Inhibits DNA synthesis (DNA polymerase) Blocks chain elongation | 200 mg po q4h 5x/day for 10 days Topical IV 5–10 mg/kg q8h |
| Ganciclovir | Purine analog | Inhibits DNA synthesis Inhibits DNA polymerase Prevents chain elongation | IV 10 mg/kg per day |
| Vidarabine | Purine analog | Inhibits DNA polymerase Prevents chain elongation | 15 mg/kg/day IV Ophthalmic oint. |
| Idoxuridine | Pyrimidine analog | Makes viral DNA more breakable | Ophth. oint. |
| Trifluridine | Pyrimidine analog | Inhibits DNA synthesis | Ophth. soln. |
| Foscarnet | Inorganic phosphonate | Inhibits viral DNA polymerase and reverse transcriptase | IV 90–120 mg/kg/day |
| Amantadine | Tricyclic amine | Blocks assembly of influenza virus | 200 mg/day |
| Rimantadine | Similar to Amantadine | Similar to Amantadine | 200–300 mg/day |
| Ribavirin | Purine analog | Multiple, including: Inhibits synthesis of guanine nucleotides Inhibits viral RNA polymerase Inhibits enzymes that cap mRNA | Aerosol 1.4 mg/kg/hr 600–1800 mg/day po 4000 mg/day IV |
| Didanosine (ddI) | Purine analog | Blocks DNA chain elongation Competitively inhibits reverse transcriptase | 125–200 mg bid po |
| Zalcitabine (ddC) | Pyrimidine analog | Inhibits viral DNA synthesis Blocks DNA chain elongation Inhibits reverse transcriptase | 0.75 mg q8h po |
| FIAU | | | |

[1]Mode of Action listed is exemplary of that generally known for each agent.
[2]Dosages provided are exemplary only. q4h = every four hours.
po = given orally.
q8h = every eight hours.
IV = intravenous
bid = given two times a day.

Antiviral agents are known and can be chemically synthesized or obtained commercially. For example: AZT, acyclovir and trifluridine (Burroughs Wellcome Co., Research Triangle Park, N.C.); ganciclovir (Syntex, Palo Alto, Calif.); vidarabine (Parke-Davis, Morris Plains, N.J.); idoxuridine (Smith Kline Beecham Pharmaceuticals, Philadelphia, Pa.); foscarnet (Astra Pharmaceuticals, Westborough, Mass.); amantadine (DuPont Pharmaceuticals (Wilmington, Del.)); rimantadine (Forest Pharmaceuticals, Maryland Heights, Mo.); ribavirin (ICN Pharmaceuticals, Inc., Costa Mesa, Calif.); didanosine (Bristol Myers Squibb Company, Evansville, Ind.); zalcitabine (Roche Products, Nutley, N.J.).

In a preferred protocol, administration of a pyrimidine or purine nucleoside analog (e.g., AZT, ddI, ddC, FIAU, acyclovir, ribavirin) at a dosage level and manner described in the Table is begun with thymosin alpha-1 at a dosage level of 1.6 mg. subcutaneously one to four times weekly, most preferably twice weekly. Antiviral therapy is continued until viral DNA levels are negative and thymosin alpha-1 is continued for an additional three months.

Measurement of severity of the disease can be accomplished in subjects. Such measurements or markers of chronic hepatitis B include the level of the enzymes ALT (alanine aminotransferase, sometimes referred to as SGPT) and AST (aspartate aminotransferase, sometimes referred to as SGOT) in the blood. These methods and techniques are standard in this art.

Below are examples of specific embodiments for carrying out the present invention. The examples are offered for illustrative purposes only, and are not intended to limit the scope of the present invention in any way.

EXAMPLE 1

A randomized, open trial with a total sample size of 20 patients is conducted. Patients included in the study are at least 18 years of age and are hepatitis B surface antigen seropositive for at least 6 months. The patients also have HBV DNA in their serum on at least two occasions at least one month apart (as measured by PCR or any other standard detection method). Only patients with chronic hepatitis B are included. These patients would have ALT levels at least 1½ times the upper limit of normal, and a liver biopsy showing changes consistent with chronic hepatitis.

Patients which have had previous therapy with interferon within one year, treatment with adrenocorticoid steroids within 6 months, HIV infection as diagnosed by HIV seropositivity and confirmed by Western blot, or the presence of hepatitis C virus antibody are excluded from the study, as well as patients who are pregnant or who have engaged in intravenous drug abuse within the previous 5 years from entering into the trial, would be excluded.

Patients will undergo a pretreatment exam monthly for at least one month prior to the treatment protocol. Examination includes:

1. Blood studies including complete blood count (CBC) with differential count, platelet count, prothrombin time (PT), chemistry panel including glucose, and creatinine, serum protein electrophoresis (SPEP), $HB_sAg$, $HB_eAg$ and HBV DNA levels, alpha-fetoprotein (AFP), $HB_eAg$ antibody, HIV antibody, HCV antibody, and hepatitis-delta antibody.
2. Liver biopsy.
3. Routine urinalysis.
4. Women of child bearing age will have a pregnancy test.

Selected patients are randomized into two groups. Group 1 will receive thymosin alpha-1 and one of the purine or pyrimidine nucleoside analogs of the present invention (e.g., ddI, ddC, AZT, FIAU, ribavirin, acyclovir). Group 2 will receive a placebo. Group 1 patients are given thymosin alpha-1 at a dosage of 1.6 mg/injection by the subcutaneous route twice weekly and ddI at a dosage of 200 mg every 12 hours orally for 6 months. Group 2 patients receive placebo injections under the same regimen. All patients are seen at 2 and 4 weeks from the start of the treatment and thereafter at monthly intervals during the 6 month treatment period. They are also monitored monthly for 6 months to one year after completion of treatment.

Response to treatment is defined by loss of serum HBV DNA or serum $HB_sAg$. A responder is a patient with decreased levels of serum HBV DNA or $HB_sAg$ achieved and sustained during the 12 month study. A nonresponder has no changes in either serum HBV DNA or $HB_sAg$ at the conclusion of the study (12 months). Relapse status is given to patients who initially lose HBV DNA in their serum but regain the DNA by the conclusion of the study.

Patients are monitored for any significant side effects or allergic manifestations resulting from the treatment. The data will be analyzed using a contingency table to compare responders and nonresponders in each group. The effect will be considered to be significant if the percentage of responders in the combination therapy group (group 1) is significantly higher than the percentage of responders in the placebo group (group 2), with a p value <0.05.

EXAMPLE 2

This protocol is similar to example 1, except the antiviral drug ddI will be given until HBV DNA levels are negative, and thymosin alpha-1 will be given for three months beyond that time.

EXAMPLE 3

These protocols are similar to examples 1 and 2, except the anti-viral drug is ddC given in a dose of 0.75 mg orally every 8 hours.

EXAMPLE 4

These protocols are similar to examples 1 and 2, except the anti-viral drug is AZT given in a dose of 200 mg orally every 4 hours.

EXAMPLE 5

These protocols are similar to examples 1 and 2, except the anti-viral drug is ribavirin given in a dose of approximately 200 mg orally every 6 hours.

Thus, methods of treating chronic hepatitis B infection are disclosed. Although preferred embodiments of the subject invention have been described in some detail, it is understood that obvious variations can be made without departing from the spirit and scope of the invention as defined by the appended claims.

What is claimed is:

1. A method for treating chronic hepatitis B infection in mammals comprising concurrently administering to a subject having chronic hepatitis B a therapeutically effective amount of at least one thymosin and an inhibitorily effective amount of interferon, either free or as a pharmaceutically acceptable salt, in a pharmaceutically acceptable vehicle.

2. The method of claim 1 wherein from about 300 $\mu$g to about 3000 $\mu$g of said thymosin per square meter of body area is administered.

3. The method of claim 1 wherein said thymosin is administered twice weekly.

* * * * *

```
                         SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
         (A) LENGTH: 28 amino acids
         (B) TYPE: amino acid
         (C) STRANDEDNESS: single
         (D) TOPOLOGY: linear (ii) MOLECULE TYPE: peptide (iii) HYPOTHETICAL: NO (vi) ORIGINAL SOURCE:
         (A) ORGANISM: Calf Thymus (xi) SEQUENCE DESCRIPTION: SEQ ID NO:1:

Ser Asp Ala Ala Val Asp Thr Ser Ser Glu Ile Thr Thr Lys Asp Leu
1               5                  10                  15

Lys Glu Lys Lys Glu Val Val Glu Glu Ala Glu Asn
              20                  25
```